United States Patent
Banko

(10) Patent No.: US 10,207,045 B2
(45) Date of Patent: Feb. 19, 2019

(54) SURGICAL HANDPIECE WITH DISPOSABLE CONCENTRIC LUMEN WORK TIP

(71) Applicant: SURGICAL DESIGN CORPORATION, Armonk, NY (US)

(72) Inventor: William Banko, Armonk, NY (US)

(73) Assignee: SURGICAL DESIGN CORPORATION, Armonk, NY (US)

( * ) Notice: Subject to any disclaimer, the term of this patent is extended or adjusted under 35 U.S.C. 154(b) by 773 days.

(21) Appl. No.: 14/506,404

(22) Filed: Oct. 3, 2014

(65) Prior Publication Data

US 2015/0025451 A1 Jan. 22, 2015

Related U.S. Application Data

(63) Continuation-in-part of application No. 14/292,459, filed on May 30, 2014, which is a continuation-in-part
(Continued)

(51) Int. Cl.
*A61M 3/02* (2006.01)
*A61F 9/007* (2006.01)
(Continued)

(52) U.S. Cl.
CPC ........... *A61M 3/0283* (2013.01); *A61F 9/008* (2013.01); *A61F 9/00745* (2013.01);
(Continued)

(58) Field of Classification Search
CPC .... A61F 2009/0087; A61F 2009/00887; A61F 9/00745; A61F 9/008; A61M 1/0064;
(Continued)

(56) References Cited

U.S. PATENT DOCUMENTS

| 4,425,115 A | * | 1/1984 | Wuchinich | ....... A61B 17/22004 310/26 |
| 4,504,264 A | | 3/1985 | Kelman | |

(Continued)

OTHER PUBLICATIONS

Non Final Office Action dated Feb. 12, 2016 in corresponding U.S. Appl. No. 14/142,555.
(Continued)

*Primary Examiner* — Brandy S Lee
(74) *Attorney, Agent, or Firm* — Leason Ellis LLP

(57) ABSTRACT

A surgical handpiece has a connecting body with a distal end and a work tip with a hub at a proximal end. The hub is detachably connected to the connecting body by a threaded connector. The work tip has an open operating end at a distal end. This opening leads an axial channel extending through the work tip from the operating end to the hub. A radial channel extends from the axial channel in the hub to the external surface of the hub. A sleeve surrounds and is spaced from the hub. This sleeve extends to the vicinity of the operating end of the work tip, and has a first external connector in the region of the radial channel of the hub. The sleeve also has a second external connector. A seal is provided for establishing a fluid connection between the radial channel of the hub and the second external connector of the sleeve. The first external connector of the sleeve is in fluid connection with an irrigation channel between the inner surface of the sleeve and the external surface of the work tip. This irrigation channel extends to the vicinity of the operating end of the work tip for delivery of irrigation fluid to that area. The irrigation channel is generally concentric with the axial channel in the hub. Aspiration fluid is withdrawn from the open operating end of the work tip, through the axial and radial channels of the hub, the seal and the second external connector of the sleeve to an aspiration pump.

15 Claims, 7 Drawing Sheets

Related U.S. Application Data of application No. 14/142,555, filed on Dec. 27, 2013, which is a continuation-in-part of application No. 12/215,315, filed on Jun. 26, 2008, now Pat. No. 8,641,658.

(51) Int. Cl.
*A61M 1/00* (2006.01)
*A61F 9/008* (2006.01)
*A61B 17/32* (2006.01)
*A61B 18/26* (2006.01)

(52) U.S. Cl.
CPC .............. *A61M 1/0064* (2013.01); *A61B 2017/320084* (2013.01); *A61B 2018/263* (2013.01); *A61B 2217/005* (2013.01); *A61B 2217/007* (2013.01); *A61F 2009/0087* (2013.01); *A61F 2009/00887* (2013.01); *A61M 2210/0612* (2013.01)

(58) Field of Classification Search
CPC ........ A61M 2210/0612; A61M 3/0283; A61M 2039/1027; A61M 2039/1044; A61M 2039/1072; A61M 39/12; A61M 39/14; A61J 1/201; A61J 1/2055; A61J 1/2065; A61J 1/2072; A61J 1/2096; A61J 1/2048; A61J 1/2082; Y10T 29/49217; A61B 2017/320084; A61B 2018/263; A61B 2217/005; A61B 2217/007
See application file for complete search history.

(56) References Cited

U.S. PATENT DOCUMENTS

| | | |
|---|---|---|
| 4,551,130 A | 11/1985 | Herbert |
| 4,735,604 A | 4/1988 | Watmough |
| 4,750,902 A | 6/1988 | Wuchinich |
| 5,084,013 A | 1/1992 | Takase |
| 5,254,082 A | 10/1993 | Takase |
| 5,817,099 A | 10/1998 | Skolik et al. |
| 6,007,511 A | 12/1999 | Prywes |
| 6,282,442 B1 | 8/2001 | DeStefano et al. |
| 6,309,347 B1 | 10/2001 | Takashi |
| 7,083,589 B2 | 8/2006 | Banko et al. |
| 7,503,895 B2 | 3/2009 | Rabiner |
| 2002/0022796 A1 | 2/2002 | Lawrence et al. |
| 2002/0161326 A1 | 10/2002 | Sussman et al. |
| 2003/0176791 A1 | 9/2003 | Rabiner et al. |
| 2005/0085769 A1 | 4/2005 | MacMahon |
| 2005/0267400 A1 | 12/2005 | Haarala |
| 2006/0173244 A1 | 8/2006 | Boulais et al. |
| 2008/0044790 A1* | 2/2008 | Fani .............. A61C 1/0015 433/119 |

OTHER PUBLICATIONS

Non Final Office Action dated Dec. 1, 2016 in corresponding U.S. Appl. No. 14/142,555.
Final Office Action dated Sep. 11, 2017 in corresponding U.S. Appl. No. 14/142,555.
Non Final Office Action dated Jul. 29, 2016 in corresponding U.S. Appl. No. 14/292,459.
Non Final Office Action dated May 18, 2017 in corresponding U.S. Appl. No. 14/292,459.
Non Final Office Action dated Jan. 26, 2018 in corresponding U.S. Appl. No. 14/142,555.

* cited by examiner

SURGICAL HANDPIECE WITH DISPOSABLE CONCENTRIC LUMEN WORK TIP

CROSS-REFERENCE TO RELATED APPLICATIONS

The present application is a continuation-in-part of prior U.S. patent application Ser. No. 14/292,459 filed on May 30, 2014, which is a continuation-in-part of U.S. patent application Ser. No. 14/142,555 filed on Dec. 27, 2013, which in turn is a continuation-in-part of prior U.S. patent application Ser. No. 12/215,315 filed on Jun. 26, 2008 (now U.S. Pat. No. 8,641,658, which issued Feb. 4, 2014). Priority is claimed only to U.S. patent application Ser. No. 14/292,459 filed on May 30, 2014, and U.S. patent application Ser. No. 14/142,555 filed on Dec. 27, 2013, both of which are incorporated herein in their entirety.

TECHNICAL FIELD

The present invention is generally directed to an ultrasonic surgical handpiece with a work tip that is disposable, and can be used for various types of surgery, e.g., the removal of cataracts from the eye of a patient by phacoemulsification.

BACKGROUND OF THE INVENTION

The use of ultrasonic and laser instruments in surgical applications is well known. One widely used type of instrument is an ultrasonic handpiece that is used in ophthalmic applications, such as in the removal of cataracts from the eye by phacoemulsification. Recently a laser device for phacoemulsification has been introduced by the A.R.C. Laser Company of Germany. Instead of ultrasonic energy, it uses a laser striking a titanium target at the tip to create emulsification.

FIG. 1 depicts a type of prior art ultrasonic handpiece as shown in U.S. Pat. No. 4,504,264 of Kelman. This handpiece has a housing 10 of, for example, plastic or metal, within which is supported a transducer means 11 for generating mechanical vibrations upon excitation with an alternating-current electrical signal. The transducer 11 is shown as a magnetostrictive transducer with an electrical coil 12 wound about a stack of metal laminations so that longitudinal mechanical vibrations are produced. The transducer can also be of the piezoelectric type.

There is a connecting body 16 of, for example, titanium, having a reduced diameter distal end portion, which also can be an attached separate portion. The connecting body forms an acoustic impedance transformer for conveying the longitudinal vibrations of the transducer 11 for application to an operative tool or working tip 14 connected to the distal end of the connecting body 16.

The work tip 14 is at least partially external of the housing 10. It is connected, such as by a screw thread, to the narrowed distal end of the connecting body 16 so as to be coupled to the transducer 11. As a result, the work tip is longitudinally vibrated by the transducer. The working tip 14 is an elongated, hollow tip of a suitable metal, such as titanium, that is capable of supporting ultrasonic vibrations. It has a distal end of a desired shape to be placed against the tissue to be removed. The work tip 14 has a threaded connector 15 in threaded engagement with the distal end of the connecting body 16. The tip 14 can be interchanged by use of the screw threads.

The distal end of the tip 14 is shown surrounded by a sleeve 17, which may be made of a material such as silicone, whose proximal end 18 is supported in threaded engagement on a reduced diameter end of the housing 10. If desired, the proximal end of sleeve 17 can be engaged more proximally along the length of the housing 10. The connecting body 16 has two elastomeric O-rings 19, 20 on its outer surface. These provide a fluid-tight seal between the connecting body 16 and the transducer means 11. A plurality of screws 51 are shown disposed around the axis of the housing 10 for preventing longitudinal displacement (other than vibration) or rotational movement of the vibratory structure within the housing and also for radial centering of the vibratory structure within the housing. Other types of conventional mounting arrangements can be used.

The handpiece also illustratively has electrical input terminals 40, 41 for applying a suitable electrical signal to the magnetostrictive transducer 11. Cooling water is shown provided inside the housing 10 from an inlet 42 to an outlet 43 and within a chamber between O-ring 19 and a grommet 50 for circulation around the transducer. This is not always necessary and is not used in most present day handpieces.

The sleeve 17 around the tip 14 forms a first fluid passage 21 between the tip 14 and the sleeve for an infusion/irrigation fluid. An inlet 22 is provided on the housing distally of the O-ring 20 for supplying the irrigation fluid to the passage 21 from a fluid supply, e.g., a bag of saline solution (not shown).

A passage 23 is formed through the connecting body 16 that is in communication with a central passage 25 of the work tip 14. An outlet 24 on the housing receives a suction (aspiration) force that is applied to the passage 23 in the connecting body and the central passage 25 in the work tip. A chamber 31 is formed between the spaced O-rings 19, 20 on the body 16 and the housing 10, with which the aspiration force from outlet 24 communicates. Thus the aspiration force is from the source (e.g., a suction pump not shown), into the chamber 31 between the O-rings, through the passage 23 in the connecting body and the passage 25 in the work tip 14. Tissue that is emulsified by the work tip is aspirated from the operating site by the aspiration flow force. In particular, saline solution introduced into the eye through fluid passage 21 and tissue displaced by the vibration force of the tip 14, is drawn into the distal end of passage 25 and passes out of the handpiece through outlet 24. It should be noted that passage 25 is located concentrically within passage 21.

As indicated, other apparatus (not shown) for use with the handpiece include the suction pump for producing the aspiration fluid (suction), the treatment fluid supply (infusion/irrigation fluid, such as a saline liquid), an oscillator for applying an electrical signal to the vibratory structure and control apparatus therefore. All of these are of conventional construction.

Considering now the operation of the handpiece of FIG. 1. When an electrical signal having a frequency of, for example, 40,000 cycles/second is applied to the coil 12 around the magnetostrictive transducer 11, the transducer 11 vibrates longitudinally at 40,000 cycles per second, thereby vibrating the connecting bodies 13, 16 and the work tip 14. Treatment fluid is supplied through inlet 22 and fluid passage 21 to bathe the tissue in the operating site region around the working tip 14. Suction force is applied through inlet 24 and passage 23 to the working tip 14 passage 25 to withdraw the tissue fragmented by the work tip along with some of the treatment fluid.

FIG. 2 is an enlarged view of the work tip of the handpiece of FIG. 1 in which the aspiration channel 25 extends axially through a major portion of the connecting body 16 and then exits the handpiece in a radial direction. FIG. 2 may also be representative of other handpieces such as the one disclosed in U.S. Pat. No. 3,589,363 of Banko et al. or ones in which the aspiration channel 25 extends completely though the handpiece.

Instruments of the type described above are often used in cataract surgery in which the eye lens is removed from the eye capsule and an intra-ocular lens (IOL) is then implanted. In such a procedure before the IOL is implanted it has been found to be desirable to cleanup lens substance and lens epithelial cells (LEC's) in the capsular bag of the eye and to remove them. Doing this procedure provides a more stable and long-term fixation for certain types of IOLs in the capsular bag. One manner of accomplishing the cleanup is to use a combination of irrigation of the capsular bag interior with a liquid together with the application of low power ultrasonic energy. This dislodges the unwanted cells and substances so that they can be removed from the capsular bag by the aspiration fluid flow.

In order to reduce the cost to patients, it is often the case that an eye surgeon will perform a large number of cataract surgeries in a single period of time. For this to be effective, the time that a surgeon spends on any one patient needs to be kept as small as possible. One time consuming procedure is the sterilization of the handpiece between surgeries on different patients. The sterilization is necessary to keep any infections that one patient has from being passed onto other patients. The aspirated fluid and cells are a source of potential infectious materials, and any part of the equipment that comes into contact with it needs to be sterilized. In the case where the aspiration channel extends completely through the handpiece, the entire handpiece needs to be sterilized. If the aspiration channel only extends through the work tip and connecting body, sterilization can be limited to those parts.

Sterilization most often takes the form of heating the handpiece in an autoclave to kill potential bacteria and viruses. However, Bovine spongiform encephalopathy or prion disease, often referred to as "mad cow" disease, is a replicating misfolded protein. Simple autoclaving may be insufficient to eliminate possibility of spreading this disease because it is viable up to about 1100° F. Certain detergent washes have to be employed for this purpose. Thus, having to extensively sterilize the equipment can greatly reduce the time required to treat a series of patients.

As shown in the present inventor's own U.S. Pat. No. 7,083,589, the surgical instrument may be provided with a coupler body located between the connecting body and the work tip. In such a case the aspiration fluid flow is provided from the work tip aspiration passage through the coupler to an outlet without coming into contact with the interior of the connecting body. Irrigation fluid can be provided through a portion of the housing that surrounds the proximal part of the work tip so as to form a chamber which is in communication with a separate passage in the work tip. The coupler is detachably connected to the connecting body. This allows the removal of the work tip, which becomes a single use part, so that the rest of the instrument can be reused by replacing the work tip without having to sterilize the connecting body. However, the portion of the housing surrounding the work tip and which forms the chamber for irrigation fluid, also needs to be replaced in this design. Thus, while the speed of treating patients can be increased by using a handpiece with disposable parts, the cost for each procedure increases because new parts are required for each patient.

Accordingly a need exists for a surgical handpiece with a relatively inexpensive disposable portion that can be discarded as a way of eliminating the need to sterilize the handpiece.

SUMMARY OF THE INVENTION

In accordance with the invention a surgical handpiece is provided that can perform all of the functions of emulsification of tissue and other substances by ultrasonic energy, aspiration of such tissue and substances, and provide liquid irrigation in which only a disposable work tip comes into contact with the aspiration fluid and needs to be changed between patients. Thus the need to dispose of or sterilize the entire work piece, the connecting body or a coupler is eliminated.

The invention provides a surgical phacoemulsification handpiece that has a novel work tip and sleeve to which the irrigation and aspiration fluids are directly connected. In particular, according to the present invention the surgical handpiece has a connecting body with a distal end that is detachably connected by a threaded connector to a hub at a proximal end of a work tip. The work tip has an opening at its distal or operating end. This opening leads to an axial channel extending through the work tip from the operating end to the hub. A radial channel extends from the axial channel in the hub to the external surface of the hub.

A sleeve surrounds and is spaced from the hub. This sleeve extends to the vicinity of the operating end of the work tip, and has a first external connector in the region of the radial channel of the hub. A seal is provided for establishing a fluid connection between the radial channel of the hub and a second external connector of the sleeve. The first external connector of the sleeve is in fluid connection with an irrigation channel between the inner surface of the sleeve and the external surface of the work tip. This irrigation channel extends to the vicinity of the operating end of the work tip for delivery of irrigation fluid to that area through its opening. The irrigation channel is generally concentric with the axial channel in the hub. Aspiration fluid is withdrawn from the opening at the operating end of the work tip. It then passes through the axial and radial channels of the hub, the seal and the second external connector of the sleeve, to an aspiration pump.

In one embodiment the sleeve is threaded onto the handpiece body. In such a case, when a new patient is to be operated on, the tubes leading to the first and second openings are removed and discarded. Then the sleeve is unthreaded from the body. Next, the threaded connector at the hub of the work tip is unthreaded from the connecting body. Both sleeve and work tip are also discarded.

Another embodiment has the sleeve permanently connected to the work tip. In that case, when the irrigation and aspiration tubes are disconnected, the work tip/sleeve unit is unscrewed from the connecting body. With this embodiment there must be a fluid tight connection between the work tip and the sleeve at the proximal end so the only path for the fluid is from the first connector to the operating end of the work tip and from the opening at the operating end through the channels in the work tip to the second connector.

By manually rotating the work tip/sleeve arrangement, the surgeon can quickly dispose of the used parts and can screw into place new parts. Thus, the time between operations on separate patients can be greatly reduced.

The principles of the invention have numerous advantages. For example, since the aspiration channel does not have to pass into a coupler or the connecting body, the handpiece can be made narrower. This makes the device easier for the surgeon to handle. The absence of this channel also provides a greater area of contact between the connecting body and the work tip, which provides greater energy transfer. Further, as noted above, the problems of sterilization are reduced and the time between surgeries can also be reduced.

BRIEF DESCRIPTION OF THE DRAWINGS

The foregoing and other objects and advantage of the present invention will become more apparent upon reference to the following specification and annexed drawings in which.

DETAILED DESCRIPTION OF THE INVENTION

Figure 3:
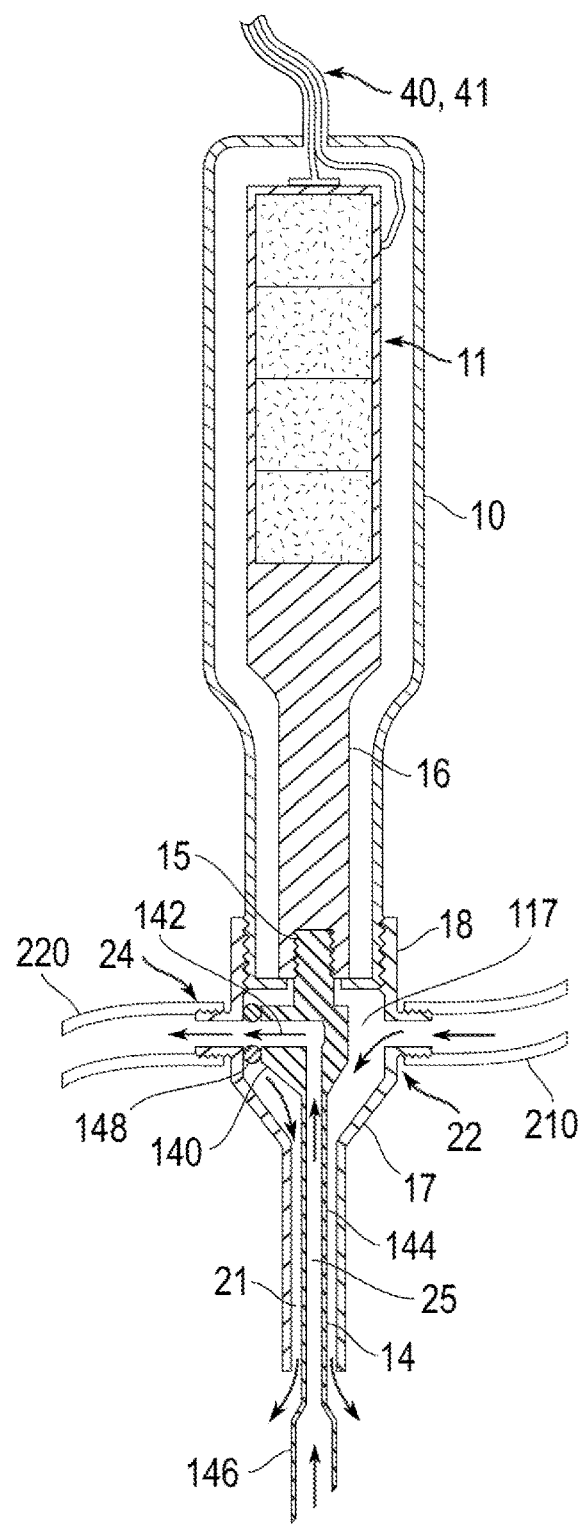
FIG. 3 is a cross section of a handpiece according to the present invention.

FIG. 3 shows an embodiment of the handpiece of the invention. It uses a number of the components of the prior art type of handpiece described above with respect to FIG. 1. The source of the electro-mechanical energy is shown schematically as transducer 11. This transducer can be either the electromagnetic type or the piezoelectric crystal type. It is preferred, and is conventional, that the output power of the transducer 11 is controlled by electrical signals delivered over wires 40, 41 from a control unit (not shown). These signals allow the ultrasonic power at the work tip distal end to be varied as needed by the surgeon.

Figure 1:
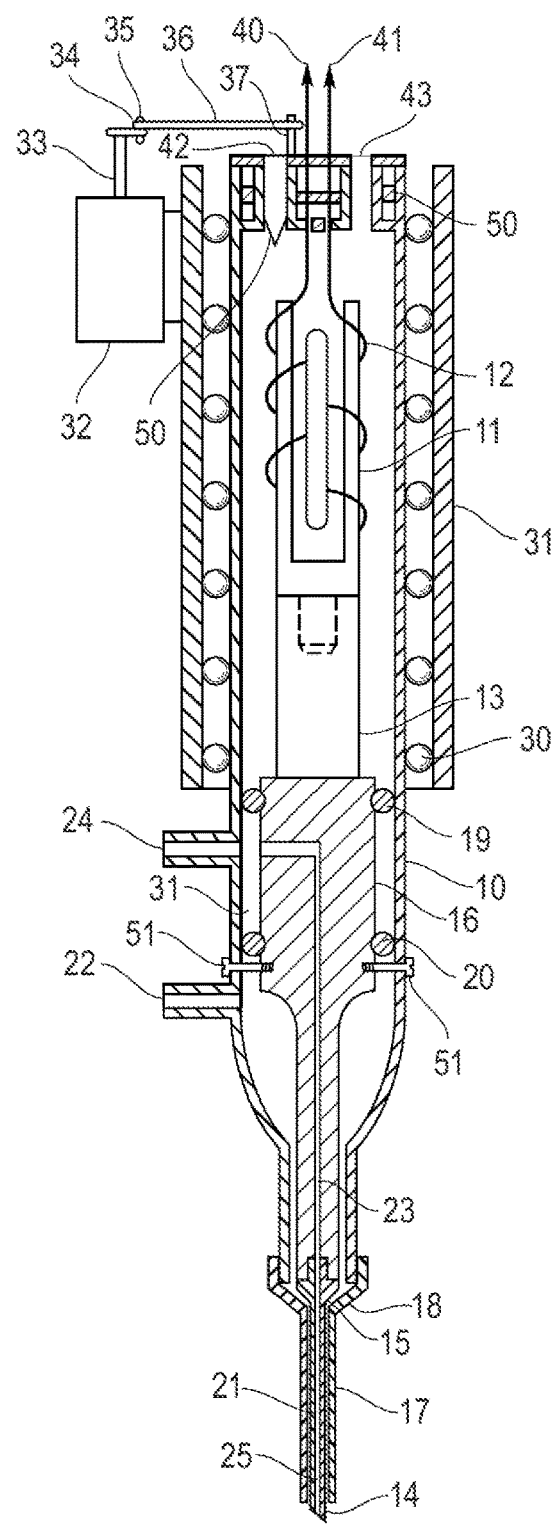
FIG. 1 is a view in cross section of a prior art type of surgical handpiece.
Figure 2:
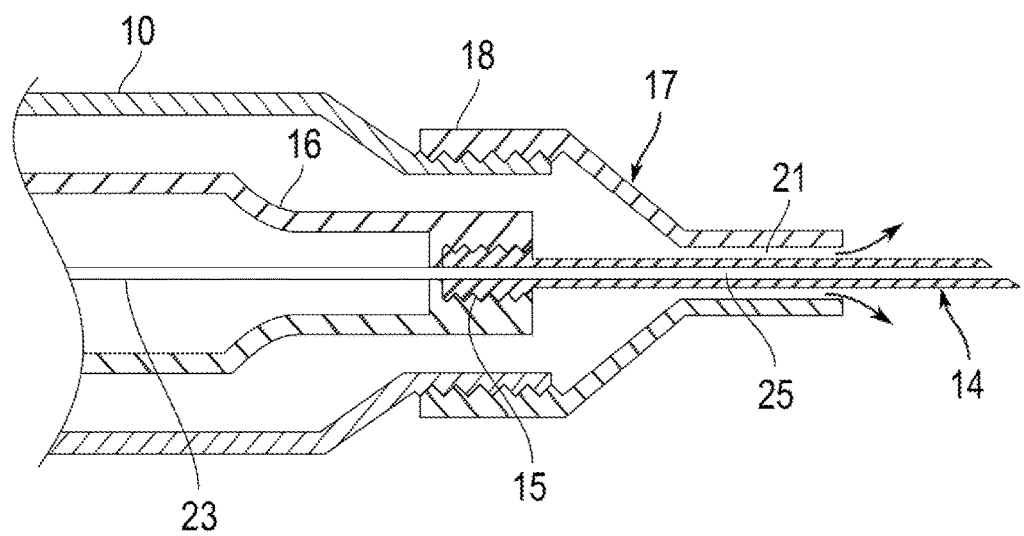
FIG. 2 is an enlarged view of the prior art type work tip of the handpiece of FIG. 1.

Connected to the transducer 11 is the connecting body 16. Both the transducer 11 and connecting body 16 are provided in a housing 10. Although not shown for the sake of clarity, the transducer and connecting body are suspended within housing 10 so as to permit the longitudinal vibration of the transducer and connecting body to occur relative to the housing. For example, the O-rings 19 and 20 shown in FIG. 1 are spaced apart around the connecting body 16 and engage the inner surface of the housing 10.

Figure 4:
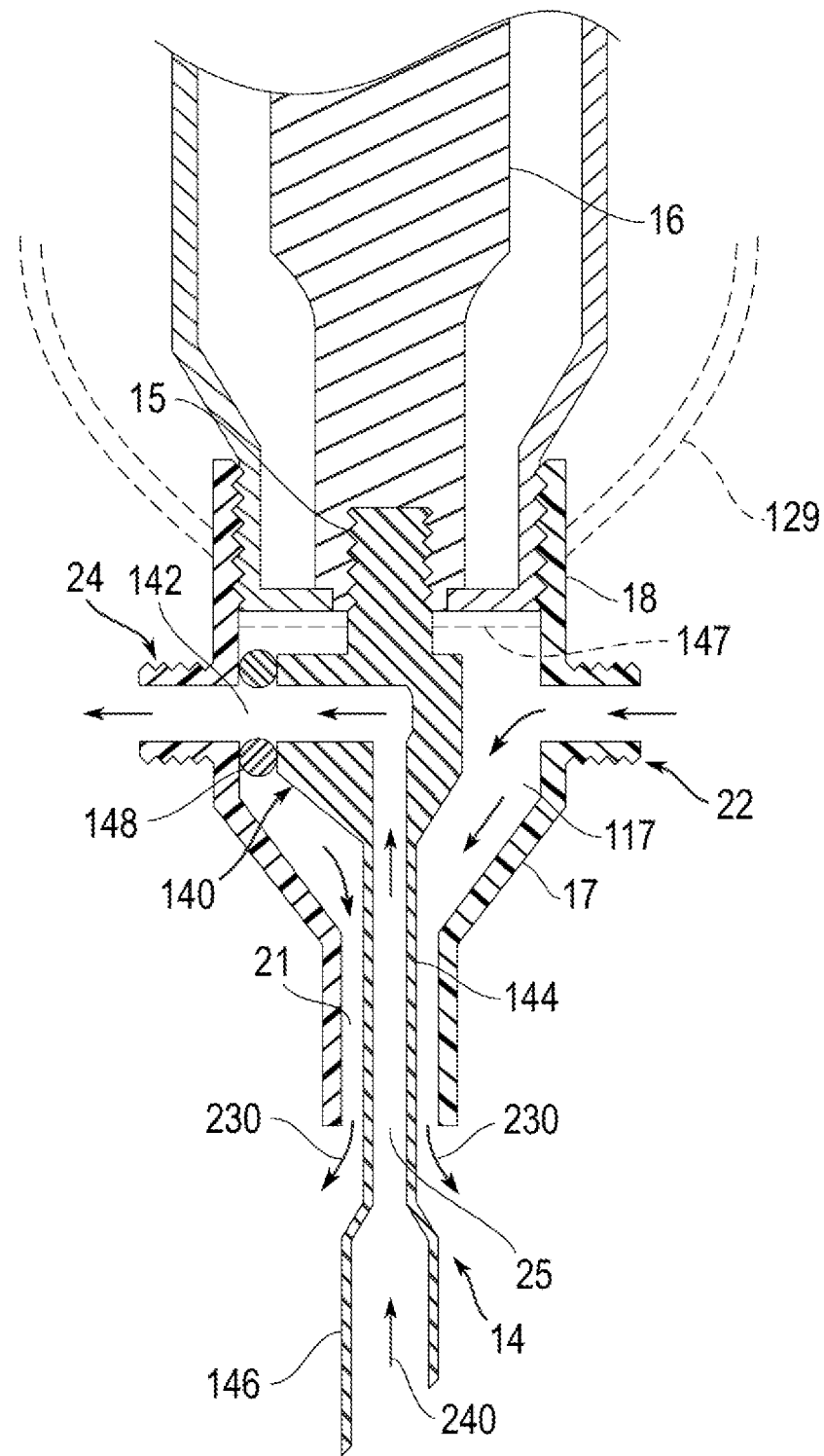
FIG. 4 is an enlarged view of the work tip of the handpiece of FIG. 3.

As best seen in FIG. 4, the work tip 14 has an opening that leads to an axial channel 25 extending from the opening to an enlarged hub 140 at the proximal end of the work tip. Within the hub 140 there is a radial channel 142 that extends from the axial channel to the outer surface of the hub. While in FIGS. 3 and 4 the radial channel 142 is shown at a right angle to the axial channel, in fact it can be at any convenient angle that allows it to extend from the axial channel to the outer surface of the hub. A threaded connector 15 extends from the proximal end of the hub and engages the distal end of the connecting body 16.

A sleeve 17, which may advantageously made of silicone, is provided with a funnel shape so that its proximal end is large enough to encompass the enlarged hub, and still leave space for chamber 117 between the outer surface of the hub and the inner surface of the sleeve. The distal end of the sleeve tapers down around the portion 144 of the work tip beyond the hub, which extends to a flared portion 146 of the work tip which is at the operating end. As a result the axial channel has a larger diameter at the operating end that tapers down to a smaller diameter as it extends through the work tip into the hub 140. The sleeve stops short of the portion 146. The proximal end 18 of sleeve 17 makes a threaded connection with the body 10 in one embodiment of the present invention.

Sleeve 17 has a first external connector 22 on its outer surface that is in fluid communication with the chamber 117. A tube 210 carrying irrigation fluid may be connected to connector 22 in order to supply irrigation fluid to chamber 117. Fluid in chamber 117 may flow between the outer surface of work tip portion 144 and the inner surface of sleeve 17 in a channel 21 so as to exit the handpiece just short of the flared portion 146 of the work tip, i.e., at the site of the operation of the handpiece on the patient's tissue. Sleeve 17 also has a second external connector 24 on its outer surface. In the drawing this connector is shown as being on the opposite side of the sleeve from the connector 22. However, in practice this connector can be at any convenient location on the sleeve. A seal piece 148, e.g., an O-ring or other form of seal, connects the radial channel 142 to the second connector 24. A tube 220 provides a suction force (e.g., from a peristaltic aspiration pump) on connector 24. This causes tissue to be drawn into the opening at portion 146 of the work tip, to travel up the axial channel 25 and into the radial channel 142, to pass through the O-ring 148 and the connector 24, and finally to be drawn through tube 220 to the aspiration pump.

In operation the handpiece of FIGS. 3 and 4 operate similar to other phacoemulsification handpieces. Electrical energy is applied through wires 40, 41, which causes the ultrasonic transduces to vibrate axially at ultrasonic frequencies. The mechanical axial force is transmitted to the connecting body 16, which in turn transmits it to the work tip 14. When the end 146 of the work tip is placed in contact with tissue, e.g., a cataract, the vibration causes the tissue to break up. While this is occurring, irrigation fluid, e.g., saline solution, passes from a source, through tube 210 and connector 22 into chamber 117, along channel 21 and is deposited at the operating site as shown by the arrows 230 in FIG. 4. At the same time the fragmented tissue is drawn into the opening in portion 146 as shown by arrow 240 in FIG. 4. It passes up the axial channel 25 into the radial channel 142, through the O-ring 148 and connector 24 to tube 220.

When the handpiece is used in its intended fashion and the procedure is over, the handpieces can be quickly readied for use on another patient without the need for sterilization. In particular, the tubes 210, 220 are disconnected and discarded. Then the sleeve 17 is unthreaded from the body at 18. Next, the work tip 14 has its threaded connector 15 loosened from connecting body 16. Then the working tip and sleeve 17 are discarded. The work tip and sleeve, as well as each of the sets of tubes are replaced with clean, pre-sterilized parts, and the handpiece is ready for the next use. This is possible because the only parts of the handpiece that come into contact with the aspiration fluid from the patient are the work tip, sleeve and the interior of tube 220. Except for the work tip, the other disposable parts can be made of inexpensive materials, e.g., silicone. Thus, the cost of the replacement parts is not very great.

Figure 5:
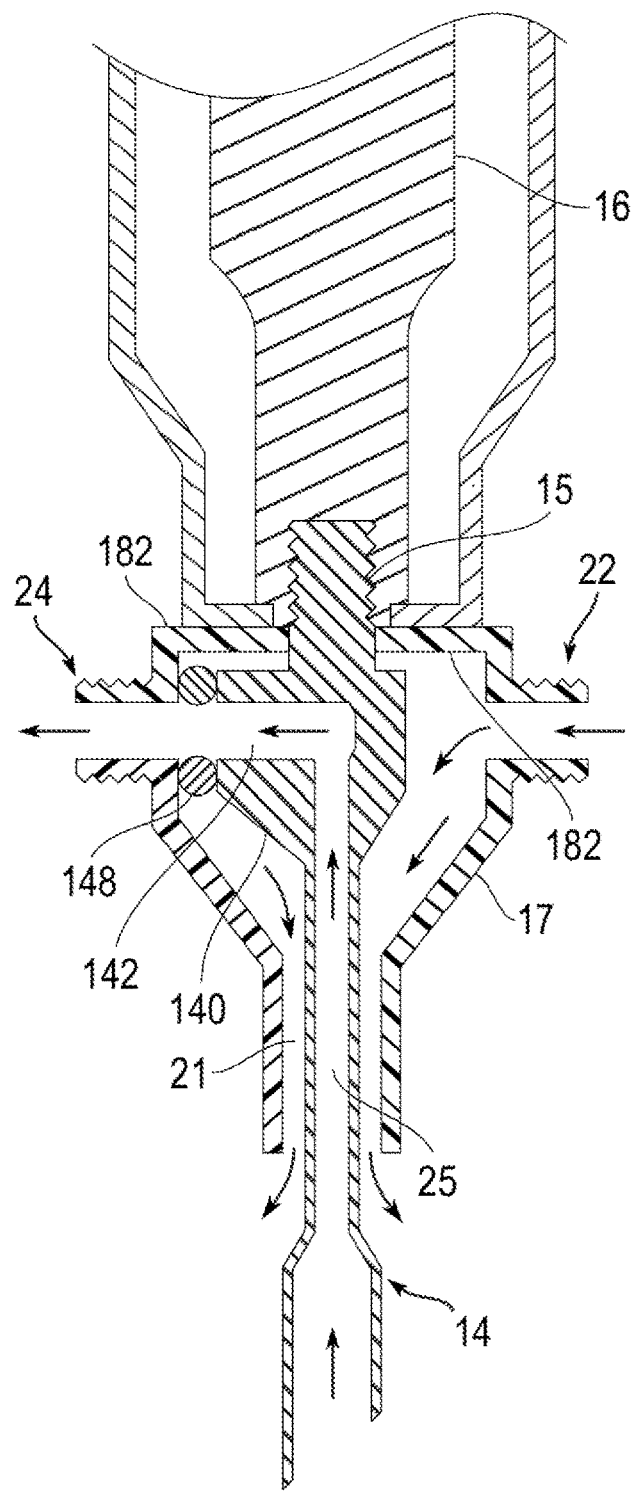
FIG. 5 an enlarged view of an alternative work tip for the handpiece of FIG. 3 wherein the work tip and sleeve form a unit.

As an alternative to the design in FIGS. 3 and 4, the sleeve can be attached to the work tip 14, and not to the body 10 as shown in FIG. 5. Here it should be noted that the proximal wall 182 of the sleeve makes a fluid tight connection with the portion of the hub 140 where the threaded connector extends. Thus, in FIG. 5, the work tip and the sleeve form an integral unit.

With the arrangement of FIG. 5, it is not necessary for the external connector 24 to be mounted on the sleeve. Instead, it can be mounted directly on the hub 140. In such a case, the sleeve does not need to extend over a major portion of the hub and the connector 22 can be moved in the distal direction. The connector 22 can also be moved on to the same side of the handpiece as the connector 24, but located distally of it.

The arrangement of FIG. 5 has the advantage in that seal 148 is stationary with respect to the work tip and there is no need to align it with the connector 24 and radial channel 142. As a result, the seal can merely be integral with the work tip and/or sleeve. Further, since by disconnecting the tubes 210, 220, the disposable parts can all be removed by twisting them as a unit so that connector 15 unscrews. Similarly, the new parts are a unit that can be installed by screwing it into the connecting body.

Figure 6:
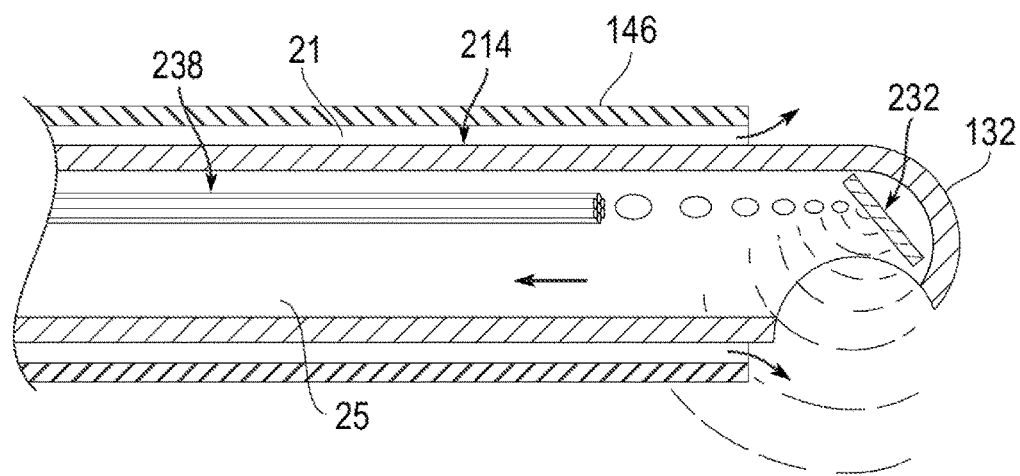
FIG. 6 is an enlarged view of a work tip that uses laser pulses to produce ultrasonic energy to emulsify the tissue.

The other embodiments rely on ultrasonic vibration for phacoemulsification. However, the breakup of tissue can also be accomplished using a laser as shown in FIG. 6. Here a work tip 214 is shown with a tube 132 that supports a fiber optic cable 238 for carrying laser light from, e.g., a YAG laser, to a titanium target 232. The effect of the light pulses hitting the target is to generate shockwaves that emulsify tissue. Tube 132 is in the axial direction. However, it extends to a work tip hub with a radial channel, such as channel 142 shown in FIG. 5. A sleeve 146 is located around the laser tube 132 so as to form the channel 21 between the inner surface of the sleeve and the outer surface of the laser tube for carrying irrigation fluid to the operating site. Tissue can be aspirated from the site by a suction force applied to tube 132.

The laser emulsifier of FIG. 6 can generally be substituted in the designs of FIG. 4 or 5. However, since mechanical vibration is not used to create the ultrasonic energy, the transducer 11 shown in FIG. 3 can be eliminated. While a handle or body 10 is still needed, there is no need for a connecting body 16. Instead, the hub can merely be screwed into a distal surface of the housing. Thus, the diameter of the housing can be reduced. An additional advantage is that because mechanical force does not have to be transmitted through the work tip, it need not be made of a strong and expensive material such as titanium. Instead, it could be made of a hard plastic. Therefore the cost of a disposable work tip can be greatly reduced.

Figure 7A:
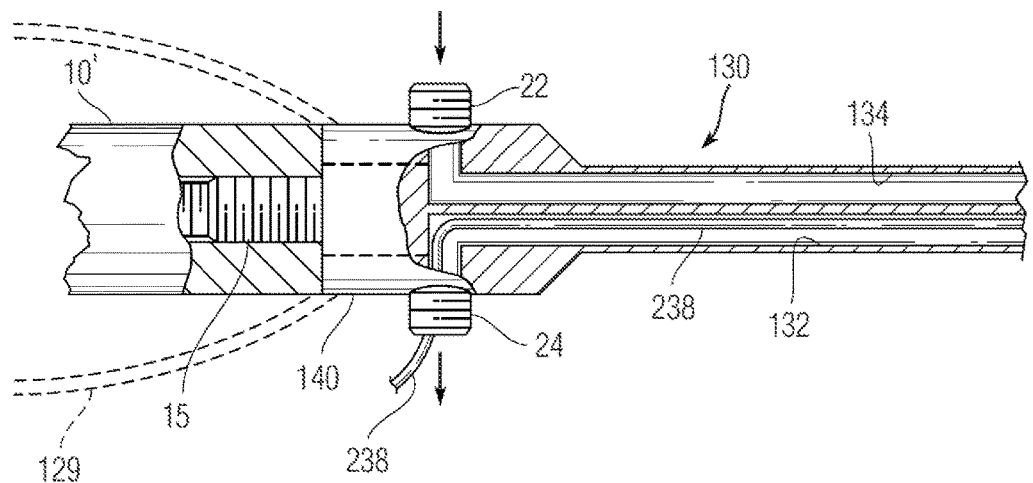
FIGS. 7A and 7B show a handpiece with dual laterally spaced tubes for delivering laser energy to the tissue in one and irrigation fluid in the other.
Figure 7B:
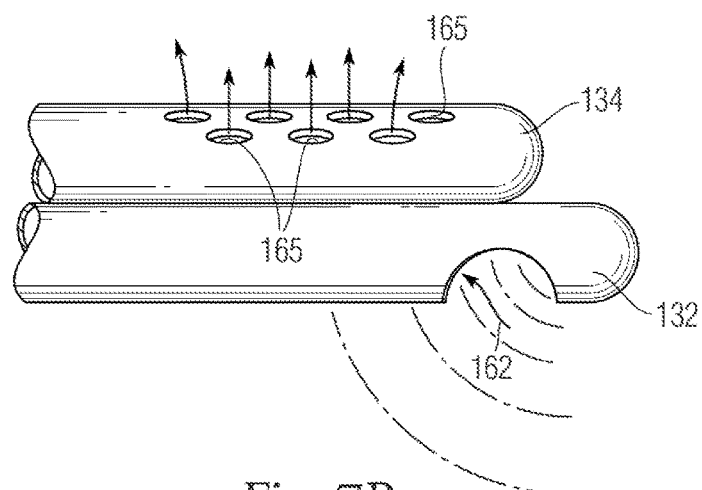

In the other embodiments shown in FIGS. 4 and 5, concentric aspiration and irrigation tubes are shown. However, FIG. 7A shows a handpiece with a work tip 130 having dual laterally-spaced tubes for (a) delivering laser energy to the tissue and aspirating the emulsified tissue pieces in one tube and (b) providing irrigation fluid in the other. As shown in FIG. 7B, tube 132 provides the laser pulses through fiber optic cable 238 and a target to create the emulsifying shockwaves. It also aspirates the tissue pieces as shown by arrow 162. Tube 134 provides irrigation fluid through holes 165.

The proximal end of the work tip 130 has connector 22 for the irrigation fluid and connector 24 for the aspiration fluid. Cable 238 may exit tube 132 through connector 24 or it may have its own separate connector. Since a laser source is used to emulsify the tissue, the housing 10' shown in FIG. 7A is made with a reduced diameter and the threaded connector 15 for the hub 140 of the work piece is screwed directly into the distal end of the housing. As shown in FIGS. 7A and 7B, the dual tube work tip 130 is disposable like the work tips 14 shown in FIGS. 4 and 5.

Since no mechanical transducers are used, the housing 10' may simply be a handle, e.g., made of inexpensive plastic. The work tip 130 can also be made of an inexpensive plastic, except for the titanium target. Thus, the work tip 130 can be discarded after a surgery or the handle and the work tip can be discarded.

In order to improve the sterile operating field, in the embodiments of FIGS. 4, 5 and 7, a sterile sheet or bag 129 can be fastened to the hub 140 of the work tip as shown in FIG. 7A. Such a sheet can also be attached to the surface 18 of the sleeve 17 in FIG. 4 or the wall 182 of the sleeve 17 in FIG. 5. With respect to the arrangement of FIG. 4, the work tip can benefit from a wall or flange 147 to help seal the sterilized environment along with the sleeve 17 and the sterile sheet 129 attached at section 18 of sleeve 17. In each embodiment the sterile sheet 129 covers the housing, and may also be used to cover any power cords used in connection with a particular embodiment. Thus, when the work tip is discarded, so is the sheet 129.

While the design of FIG. 7A is for the laser generated ultrasonic energy of emulsification, it could also be used with a mechanically generated ultrasonic emulsifier having transducers 11 as shown in FIG. 3, but without fiber optic cable 238. In such a case, beneficial use can also be made of the sterile sheet 129, with it being attached to hub 140.

While the invention has been shown and described in connection with the removal of cataract from the eye of a patient, the apparatus and method may also be used for other types of surgery in other parts of the body, e.g., the removal of neurological tissue.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the scope of the appended claims.

I claim:

1. A surgical handpiece comprising:
   a connecting body having a distal end;
   a work tip having an open operating end at a distal end thereof and an axial channel extending there through;
   a hub connected to a proximal end of the work tip, said hub having a threaded connector for detachably attaching the hub to the connecting body, a hub axial channel formed by the hub and connected to the work tip axial channel at the proximal end of the work tip and a radial channel formed by the hub and extending at an angle from the hub axial channel to an external surface of the hub;

a sleeve surrounding and spaced from the hub, said sleeve extending to the vicinity of the open operating end of the work tip, said sleeve having a first external connector;

a second external connector connected to the radial channel of the hub; and a seal for establishing fluid connection between the radial channel of the hub and the second external connector; and wherein the first external connector of the sleeve is in fluid connection with an irrigation channel between an inner surface of the sleeve and the external surface of the work tip which extends to the vicinity of the open operating end of the work tip for delivery of irrigation fluid to that vicinity of the open operating end of the work tip, said irrigation channel being generally concentric with the axial channel in the hub; and wherein aspiration fluid is withdrawn from the open operating end, through the hub axial channel, the radial channel of the hub, the seal and the second external connector.

2. The surgical handpiece according to claim 1 wherein the work tip and the sleeve are designed to be disposable after an operation.

3. The surgical handpiece according to claim 1 further including a housing for the handpiece and wherein the sleeve is in threaded engagement with the housing.

4. The surgical handpiece according to claim 1 further including a housing for the handpiece and wherein the sleeve is not in threaded engagement with the housing, said sleeve forms an integral unit with the work tip and is in fluid tight engagement with the proximal end of the work tip.

5. The surgical handpiece according to claim 4 wherein the seal is part of the integral unit.

6. The surgical handpiece according to claim 4 further including a sterile sheet attached to a proximal portion of the work tip so as to cover the housing, said sterile sheet being part of the integral unit.

7. The surgical handpiece according to claim 6 further including a sterile sheet attached at the proximal portion of the integral unit.

8. The surgical handpiece according to claim 4 further including a flange at the threaded connector of the work tip to improve sterile conditions at the work tip.

9. The surgical handpiece according to claim 1 wherein the second external connector is mounted on the sleeve.

10. The surgical handpiece according to claim 1 further including a sterile sheet attached at a proximal portion of the hub of the work tip so as to cover the housing.

11. The surgical handpiece according to claim 1 further including a sterile sheet attached at a proximal portion of the sleeve so as to cover the housing.

12. A surgical hand-piece comprising: a handle, a work tip mounted for ultrasonic vibration, a hub connected at a proximal end of the work tip, said work tip having an open operating end at a distal end thereof, said hub having an externally threaded connector for detachably attaching the hub to an internally threaded cavity in the handle, a work tip axial channel for aspiration fluid flow extending through the work tip from the open operating end to a hub axial channel formed by the hub and a radial channel formed by the hub that extends at an angle from the hub axial channel in the hub to an external surface of the hub.

13. The surgical hand-piece of claim 12 further including a fiber-optic cable extending along the work tip axial channel to the open operating end, and a target at the open operating end of the work tip axial channel such that contact between a laser beam traveling through the fiber optic cable and the target is adapted to cause shockwaves that emulsify tissue.

14. The surgical hand-piece of claim 13 further including a sleeve surrounding and spaced from the work tip, said sleeve extending to the vicinity of the open operating end of the work tip, a channel formed between the inner surface of the sleeve and the outer surface of the work tip adapted for carrying irrigation fluid to the open operating end, and the work tip axial channel adapted for aspirating tissue from the operating end.

15. A work tip mounted for ultrasonic vibration, a one piece hub connected at a proximal end of the work tip, said work tip having an open operating end at a distal end thereof, said hub having an externally-threaded connector for detachably attaching the hub to an internally threaded cavity in a handle, a work tip axial channel for aspiration fluid flow extending through the work tip from the open operating end to a hub axial channel formed by the hub and a radial channel formed by the hub that extends at an angle from the hub axial channel in the hub to an external surface of the hub, said work tip axial channel of the work tip having a larger diameter portion at the operating end, a taper portion that tapers down to a smaller diameter portion which is about the size of the hub axial channel, the smaller diameter portion extends from the taper portion over a distance and to the hub axial channel.

* * * * *